(12) United States Patent
Ochoa et al.

(10) Patent No.: US 9,617,845 B2
(45) Date of Patent: Apr. 11, 2017

(54) RESONATOR ASSEMBLY LIMITING MAGNETIC PARTICLE ACCUMULATION FROM WELL FLUIDS

(71) Applicant: BAKER HUGHES INCORPORATED, Houston, TX (US)

(72) Inventors: Brian B. Ochoa, Hannover (DE); Thomas Kruspe, Niedersachsen (DE)

(73) Assignee: BAKER HUGHES INCORPORATED, Houston, TX (US)

( * ) Notice: Subject to any disclaimer, the term of this patent is extended or adjusted under 35 U.S.C. 154(b) by 117 days.

(21) Appl. No.: 14/512,090

(22) Filed: Oct. 10, 2014

(65) Prior Publication Data

US 2016/0102547 A1 Apr. 14, 2016

(51) Int. Cl.
*E21B 47/10* (2012.01)

(52) U.S. Cl.
CPC .................. *E21B 47/101* (2013.01)

(58) Field of Classification Search
CPC ..................................................... E21B 47/101
See application file for complete search history.

(56) References Cited

U.S. PATENT DOCUMENTS

| | | | |
|---|---|---|---|
| 6,397,661 B1 | 6/2002 | Grimes et al. | |
| 6,668,230 B2 | 12/2003 | Mansky et al. | |
| 6,910,257 B1 * | 6/2005 | Gorohata | H02K 15/0428 242/599.1 |
| 7,350,367 B2 | 4/2008 | Matsiev et al. | |
| 7,357,016 B2 | 4/2008 | Kurowski et al. | |
| 7,437,912 B2 | 10/2008 | Sparks et al. | |
| 7,552,619 B2 | 6/2009 | Andle | |
| 7,878,044 B2 | 2/2011 | Andle | |
| 2002/0178805 A1 | 12/2002 | DiFoggio et al. | |
| 2007/0052970 A1 | 3/2007 | Kolosov et al. | |

(Continued)

FOREIGN PATENT DOCUMENTS

| | | |
|---|---|---|
| EP | 2596328 A2 | 1/2012 |
| GB | 1536285 A | 12/1978 |
| WO | 2012122482 A2 | 9/2012 |

OTHER PUBLICATIONS

Int'l Search Report & Written Opinion in PCT/US2016/054635, dtd Jan. 7, 2016.

*Primary Examiner* — Ryan Walsh
(74) *Attorney, Agent, or Firm* — Mossman Kumar & Tyler PC

(57) ABSTRACT

Systems, devices and methods for determining a parameter of interest of a well fluid relating to a well intersecting a subterranean formation using resonant vibration. The apparatus may include a resonator assembly. The resonator assembly may comprise a plurality of resonant tines structurally coupled to behave as a single resonator. At least one resonant tine of the plurality of resonant tines may include a soft magnetic tine head comprising soft magnetic material uncontained by a supporting surface. Each corresponding tine of the plurality of resonant tines may be formed by at least the resonant tine head and a tine shaft. Each corresponding tine may have a cross section perpendicular to a longitudinal axis of the corresponding tine, the cross section including a tine head, where the cross section has a substantially continuous material composition. Each tine shaft may terminate at the tine head.

20 Claims, 11 Drawing Sheets

(56) References Cited

U.S. PATENT DOCUMENTS

| | | |
|---|---|---|
| 2007/0296410 A1* | 12/2007 | Blumberg .............. G01R 33/02 324/244 |
| 2010/0015649 A1 | 1/2010 | Day |
| 2012/0085161 A1 | 4/2012 | Kumar |
| 2012/0227483 A1 | 9/2012 | Kruspe et al. |
| 2013/0139576 A1 | 6/2013 | Goodbread et al. |
| 2013/0191046 A1 | 7/2013 | Henning et al. |

* cited by examiner

RESONATOR ASSEMBLY LIMITING MAGNETIC PARTICLE ACCUMULATION FROM WELL FLUIDS

FIELD OF THE DISCLOSURE

This disclosure relates generally to exploration and development of underground formations and more particularly to systems and methods for sampling and testing well fluids within a borehole or in a production system.

BACKGROUND

Commercial development of hydrocarbon fields requires significant amounts of capital. Before field development begins, operators desire to have as much data as possible in order to evaluate the reservoir for commercial viability. It is often desirable to conduct testing of the hydrocarbon reservoirs in order to obtain useful data. Therefore, during drilling or after a borehole for a well has been drilled, hydrocarbon zones are often tested with tools that characterize fluid samples, e.g., liquids from downhole. Some of these tools may be at the surface. Testing may be carried out during several phases of wellbore development. In some cases, fluids are tested to facilitate drilling or completing the wellbore. During and after the formation of the borehole, fluid characteristics may used directly or indirectly for estimating the presence of producible formation fluids (e.g., petroleum). Once the well is in production, fluid parameters related to well production provide further data relating to the yield of the formation. Information about the wellbore or the formation obtained from fluid testing facilitates proper management of the well in this stage, which is vital to optimizing long-term production.

SUMMARY OF THE DISCLOSURE

In aspects, the present disclosure includes an apparatus for determining a parameter of interest of a well fluid relating to a well intersecting a subterranean formation using resonant vibration. The apparatus may include a resonator assembly. The resonator assembly may comprise a plurality of resonant tines structurally coupled to behave as a single resonator. At least one resonant tine of the plurality of resonant tines may include a soft magnetic tine head comprising soft magnetic material uncontained by a supporting surface. The apparatus may be used for determining a parameter of interest of a well fluid from a subterranean formation. Each corresponding tine of the plurality of resonant tines may be formed by at least the resonant tine head and a tine shaft. Each corresponding tine may have a cross section perpendicular to a longitudinal axis of the corresponding tine, the cross section including a tine head, where the cross section has a substantially continuous material composition. Each tine shaft may terminate at the tine head. The soft magnetic material may have a compressive strength of at least 200 MPa. The tines may be substantially parallel or non-parallel. The apparatus may comprise a coating for the soft magnetic resonant tine heads.

The resonator assembly may include a switchable biasing assembly that, when activated, provides a magnetic bias field that magnetizes the soft magnetic tine head of the at least one resonant tine; and a switchable drive assembly that, when activated, acts on the magnetized soft magnetic head of the at least one resonant tine to cause resonant vibration of the magnetized soft magnetic head of the at least one resonant tine. The apparatus may include a processor configured to: activate the switchable biasing assembly and the drive assembly; sense the vibration of the magnetized soft magnetic tine head of the at least one resonant tine in a flow of the downhole fluid; and determine the parameter based on the sensed vibration.

The apparatus may include a magnetic yoke having a central passage, wherein the apparatus is configured to produce flux paths for at least one of the switchable biasing assembly and the drive assembly such that more than half of the total flux for the switchable biasing assembly and the drive assembly lies inside the central passage. The apparatus may include at least one magnetic yoke, wherein at least one of the switchable biasing assembly and the drive assembly is positioned between the tine heads and at least a portion of the at least one magnetic yoke. The apparatus may include at least one magnetic yoke encircling the switchable biasing assembly, the drive assembly, and the soft magnetic resonant tine heads. The at least one magnetic yoke may act on a magnetic field of the drive assembly and/or a magnetic field of the switchable biasing assembly to increase torque acting on the soft magnetic resonant tine head of the at least one resonant tine during the resonant vibration. The magnetic yoke may act on a static magnetic field of the switchable biasing assembly to increase magnetization on the soft magnetic resonant tine head of the at least one resonant tine during activation of the biasing assembly.

The apparatus may include a conduit, wherein while the apparatus is immersed in the fluid, the fluid enters a first end of the conduit and flows along the conduit to a second end of the conduit, and the soft magnetic resonant tine head of the at least one resonant tine is in a flow of the fluid in the conduit. The soft magnetic tine head of the at least one resonant tine may be oriented so that the longitudinal axis of the tines is substantially parallel to the flow of the fluid. The apparatus may be further configured to carry out methods of the present disclosure, as described below.

In aspects, the present disclosure provides methods of determining a parameter of interest of a well fluid relating to a well intersecting a subterranean formation using resonant vibration. The method may include activating a switchable biasing assembly to provide a magnetic bias field that magnetizes at least one soft magnetic tine head coupled to a corresponding one of a plurality of resonant tines structurally coupled to behave as a single resonator, and each soft magnetic tine head comprising soft magnetic material uncontained by a supporting surface; activating a switchable drive assembly to act on the at least one magnetized soft magnetic head to cause resonant vibration of the at least one magnetized soft magnetic head; sensing the vibration of the at least one magnetized soft magnetic head in a flow of the downhole fluid; and determining the parameter based on the sensed vibration. The method may include cleaning the magnetized soft magnetic heads by Gaussian demagnetization caused by deactivating the switchable biasing assembly. The method may include cleaning the soft magnetic tine heads by removing particles using a fluid comprising at least one of: i) the downhole fluid; and ii) engineered fluid. The soft magnetic heads may be switchable between a magnetic state producing a magnetic field and a non-magnetic state producing substantially no magnetic field. The downhole fluid may comprise production fluid.

Examples of certain features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals.

DETAILED DESCRIPTION

Figure 1A:
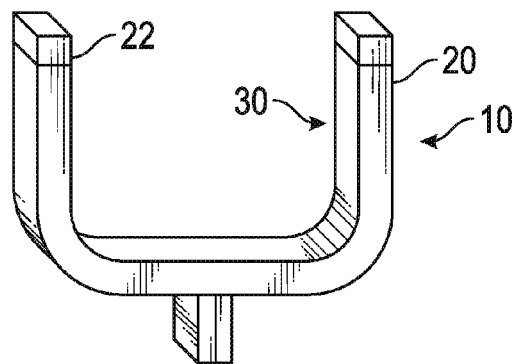
FIGS. 1A-1I show resonators for determining a parameter of interest of a well fluid using resonant vibration in accordance with embodiments of the present disclosure.
Figure 1B:
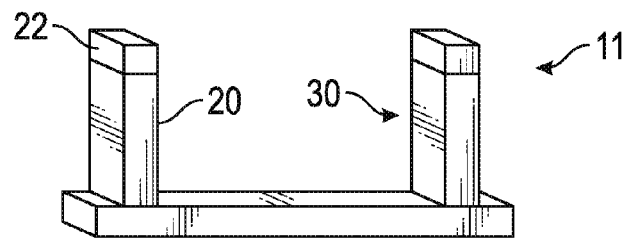
Figure 1C:
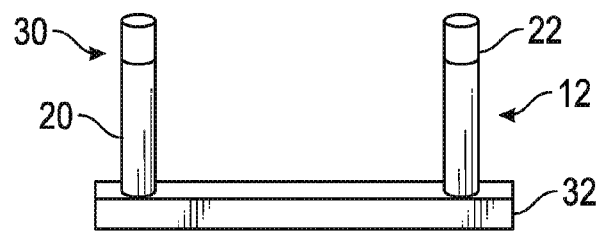
Figure 1D:
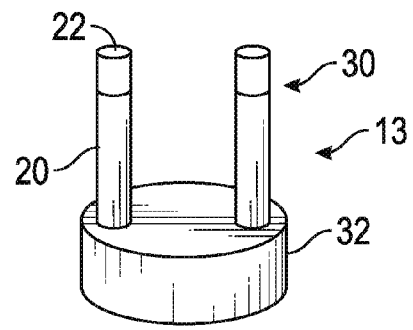
Figure 1E:
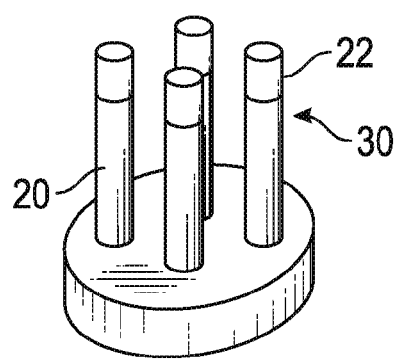

In aspects, the present disclosure relates to devices and methods for evaluating well fluids relating to a subterranean earth formation. In a first general embodiment, the fluid may be evaluated in a borehole intersecting an earth formation, including, in some cases, in situ. In other general embodiments, the present disclosure relates to devices and methods for evaluating a well fluid recovered via a wellbore intersecting an earth formation or introduced to a wellbore. The well fluid may be a hydrocarbon fluid.

It is possible to use resonant sensors to estimate various properties of well fluids, particularly in downhole environments. Determining the acoustic properties of downhole fluids may be desirable for several types of downhole evaluation. Such properties may be used in characterizing the fluid itself, or for use in methods for evaluating the formation, the borehole, the casing, the cement, or for previous or ongoing operations in the borehole including exploration, development, or production. In one example, characteristics of the fluid may be correlated with observed characteristics of the motion of a resonator at one or more frequencies of vibration, including at or near a resonant frequency. Characteristics of the motion, including the resonant frequency of the resonator while immersed in the fluid, attenuation of the motion, and electrical characteristics required for the driving electronics to meet the resonant frequency or maintain a pre-set frequency may be used to estimate fluid characteristics such as density, dielectric constant, and viscosity of the fluid. For example, depending upon the viscosity of the fluid, the resonant frequency of the resonator changes in a predictable manner, which allows the viscosity of the fluid to be estimated using a model correlating the resonant frequency to the density of the fluid. Viscosity and density may then be used to estimate gas/oil ratio and calculate permeability of the formation.

As another example, it is known to conduct acoustic inspection of a casing cemented in a borehole to determine specific properties related to the casing and surrounding materials. For example, the bond between the cement and the casing may be evaluated, or the strength of the cement behind the casing or the casing thickness may be estimated using measurements of reflected acoustic waves, which may be generally referred to as casing cement bond logging. For many of these techniques, it is desirable that variations in fluids filling the borehole (e.g., drilling fluid) be compensated for, because conventional processing is highly sensitive to the properties of the drilling fluid.

Thus, various techniques are currently employed to determine parameters of the fluid affecting acoustic measurements, such as acoustic impedance and sound speed in order to interpret the acoustic reflection data.

Resonant members of the sensor may be excited in proximity to a resonant frequency while immersed in a well fluid. The vibrational response of the resonant members to the fluid (e.g., vibrational characteristics while in the fluid) may be sensed to provide information relating to fluid characteristics, such as, for example, density, viscosity, sound speed, acoustic impedance, and so on. For example, dividing the fluid acoustic impedance by the fluid density, the fluid sound speed may be obtained. This information may then be used to estimate various parameters of interest of the fluid, the formation, casing, and so on. Traditionally, such sensors may be used as part of an instrument in measurement-while-drilling ('MWD') or wireline tools to measure properties of a downhole fluid. As one example, the fluid may be acquired in a sample chamber of the tool. The instruments may be subject to considerable forces and pressures as part of the downhole tool, which may affect measurement accuracy and precision and materially affect design considerations.

Resonators using structurally coupled resonant tines are known. Flexural mechanical resonators (e.g., a tuning fork) are one example. The tines of the resonator may be excited and/or measured using electromagnetic mechanisms. One reason for the adoption of this technology by the industry is that it is feasible to manufacture tines with appropriate resonant characteristics from durable, corrosion resistant materials that can withstand the downhole environment.

More recently, permanent magnets in the resonator tine ends may be used to excite vibration and provide a magnetic signal of the resonance response (e.g., resonance frequency and damping). As one example, permanent magnets embedded in the heads of the tines may be acted on by an electromagnetic coil assembly to generate resonant vibration. Various configurations are possible to produce various types of motion in the tine heads. The response may be detected via a voltage induced in a sense coil, which in some cases may be the same coil used to drive the vibration. This voltage may be used to monitor the characteristics of vibration (e.g., vibrational amplitude and phase) to derive information relating to properties of the fluid. In some implementations, this may be carried out by exciting the tuning fork to resonance, switching off the excitation, and then measuring the decay. Additionally or alternatively, other types of sensing apparatus may used to monitor the characteristics of vibration of the tines. For a variety of reasons, magnetic tine heads have proven to be beneficial in measuring downhole fluid properties.

In some cases, downhole fluids contain magnetic particles coming from pipe scale, wear of steel components, corrosion, mud additives, and the like. These particles adhere to magnetic tine heads. The measurement techniques described above using magnets in the tine heads may have great sensitivity with respect to magnetic particles. That is, when magnetic particles accumulate on the tines, the results of measurements are tainted. For example, a mechanical resonator will provide inaccurate and/or imprecise results when magnetic particles attach to the permanent magnets of the tine tips, due to a change in resonance characteristics. Moreover, once attached, removing the magnetic particles from the tines may be difficult and time consuming.

Self Cleaning

Particular aspects of the present disclosure minimize, if not eliminate, magnetic particles fouling of the tines. Method aspects may further include estimating a parameter of interest of the well fluid using measurements from the instruments. Illustrative techniques according to this disclosure employ a resonator having a switchable magnetic head to ensure that magnetic particles do not accumulate on the head where they may interfere with instrument measurements. Further aspects of the disclosure include elements that facilitate cleaning of the heads or improve the sensor response.

Device embodiments include an apparatus for determining a parameter of interest of a well fluid from a subterranean formation using resonant vibration. The apparatus may include a resonator assembly comprising at least two resonant tines structurally coupled to behave as a single resonator. Each resonant tine of the at least two resonant tines includes a soft magnetic tine head comprising soft magnetic material uncontained by a supporting surface. A soft magnetic material may be defined as one with little remnant magnetization in the absence of a magnetic field. The magnetic hysteresis loop for such a material may thus be narrow, and coercivity is low (less than 450 A m$^{-1}$) while permeability is high (greater than 800). For example, the soft magnetic material may be a corrosive resistant alloy.

The soft magnetic tine head is thus switchable between a magnetic state producing a magnetic field and a non-magnetic state producing substantially no magnetic field. In operation, a direct current from power source may be applied to a coil to generate a magnetic field biasing the soft magnetic tine head to a magnetic state. While in the magnetic state, the tine heads may be driven by an electromagnetic assembly (e.g., a coil having an alternating current applied). The current can be switched on periodically for as long as needed to measure fluid properties of the well fluid. Once measurements are completed, the biasing coil may be deactivated by removing the current, which allows the soft magnetic material to return to a non-magnetized state. Soon after the current is switched off, substantially no magnetization remains in the soft magnetic tine heads, and any caught magnetic particles are released. The released particles may then be flushed from the head using a fluid (e.g., the tested fluid).

Although soft magnetic material inserts ('plugs') are known, the soft magnetic material is contained by a structural surface to resist corrosion and insure structural integrity of the tine. The effect of the supporting structural material, such as, for example, inconel, in previous sensors is to limit the size of available soft magnetic material which may react to the bias and driving fields, and thus limit the sensor response to a problematic degree. In contrast to embedded soft magnetic inserts in the tine body, embodiments of the present disclosure may implement the resonator using soft magnetic materials as substantially the entire tine head and uncontained by structural surfaces. The uncontained tine head dramatically increases the sensor response and thus avoids the issues of tines using imbedded soft magnetic materials.

By minimizing magnetic particle accumulation, aspects of the present disclosure enable the use of magnetically driven tine heads in applications where fluid filtration is not possible or the sensor is deployed for extended periods without maintenance ('permanently'). Device embodiments may be employed to perform measurements on downhole well fluids or well fluids recovered via a borehole, such as, for example, production fluids, or other oil field chemicals.

Figure 1F:
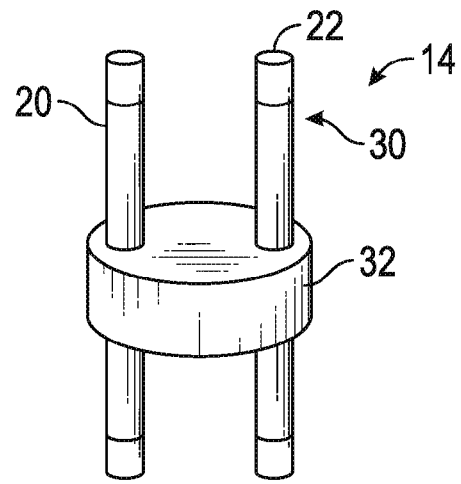
Figure 1G:
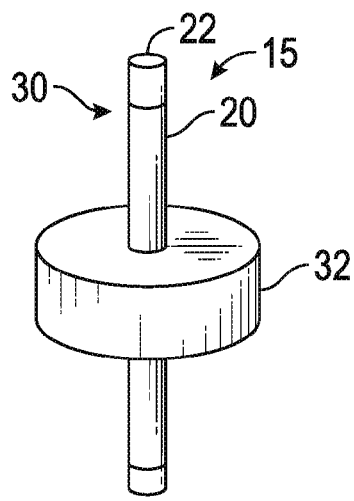
Figure 1H:
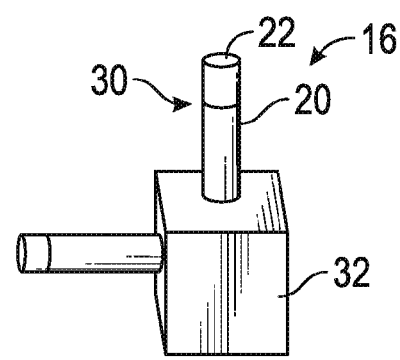
Figure 1I:
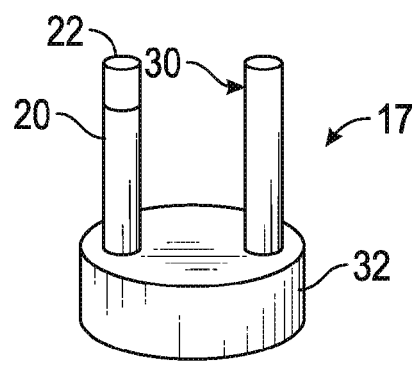

FIGS. 1A-1I show resonators 10-17 for determining a parameter of interest of a well fluid from a subterranean formation using resonant vibration in accordance with embodiments of the present disclosure. Each resonator includes at least one pair of tines 30 structurally coupled to behave as a single resonator. In some implementations, this is accomplished by affixing the tines 30 to a resonator body 32, which may be substantially perpendicular to the axis of one or more tines 30. For FIGS. 1A-1H, each tine 30 includes a tine shaft 20 and a soft magnetic tine head 22 uncontained by a supporting surface. The tine heads 22 may have treatments, coatings, or other non-structural coverings applied, however. FIG. 1I includes only one soft magnetic tine head 22. Thus, although the tines 30 are structurally coupled to behave as a resonator, only the tine with the soft magnetic head is directly driven. FIGS. 1F & 1G illustrate coaxially mounted tines 20 with tine heads 22 at opposite ends of the resonator. FIG. 1H illustrates non-parallel tines 20. Each of the various embodiments will have corresponding advantages and disadvantages which will recommend its use in particular applications in accordance with particular design specifications.

The tine head 22 is made up of soft magnetic material, described in further detail with respect to FIG. 2C below. The tine shaft may terminate at the tine head 22. The tine head 22 may be coupled to the tine shaft 20 through the use of adhesives, welding, or the like. Other techniques for coupling may be used in particular embodiments, such as, for example, tines shown in FIGS. 2A & 2B, which may be mechanically coupled in addition to or instead of adhesively coupled.

Figure 2A:
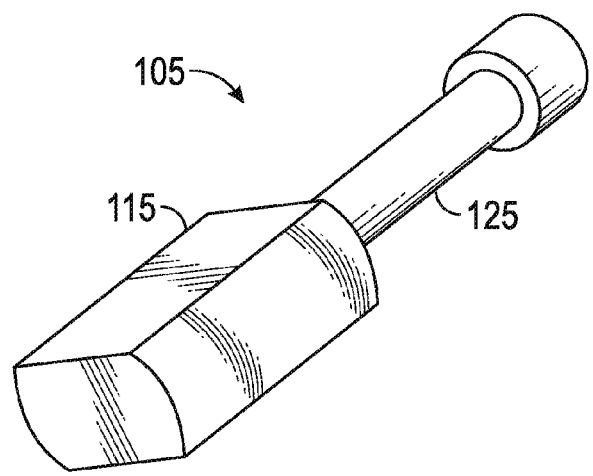
FIG. 2A shows a resonator tine of an instrument for determining a parameter of interest of a well fluid using resonant vibration in accordance with embodiments of the present disclosure.
Figure 2B:
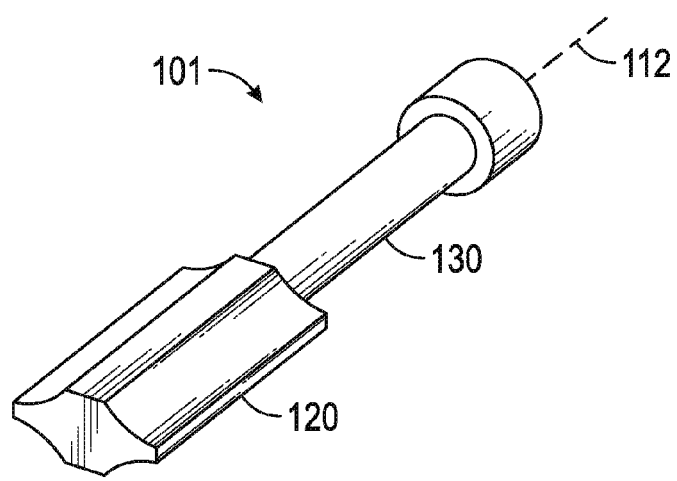
FIG. 2B shows another resonator tine of an instrument for determining a parameter of interest of a well fluid using resonant vibration in accordance with embodiments of the present disclosure.
Figure 2C:
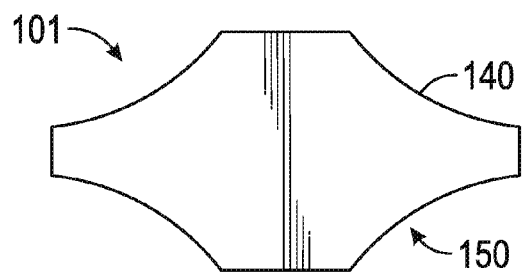
FIG. 2C shows a cross section of a tine through the tine head in accordance with embodiments of the present disclosure.

FIG. 2A shows a resonator tine 105 of an instrument for determining a parameter of interest of a well fluid from a subterranean formation using resonant vibration in accordance with embodiments of the present disclosure. FIG. 2B shows another resonator tine 110 of an instrument for determining a parameter of interest of a well fluid from a subterranean formation using resonant vibration in accordance with embodiments of the present disclosure.

Resonator tines 105,110 are configured for coupling to a resonant body (shown below with respect to FIGS. 7A & 7B). Each tine 105,110 is formed by at least a tine head 115, 120 and a tine shaft 125, 130, respectively. Various tine head designs different tine head dimensions will occur to those of skill in the art, and will have associated advantages and disadvantages. Tine heads may be beveled to reduce moment of inertia. In particular embodiments, the tine shaft 125, 130 may have a significantly narrower cross section than that of the tine head 115, 120. FIG. 2C shows a cross section 101 of tine 110 through the tine head 120. The cross section, which is perpendicular to a longitudinal axis 112 of tine 110 and includes tine head 120, has a substantially continuous material composition, comprising the soft magnetic material 140.

Soft magnetic material 140 may have high corrosion resistance suitable for contact with downhole fluids in downhole environmental conditions. Soft magnetic material 140 may have a tensile strength of at least 200 MPa to be suitable for the mechanical demands of the resonator. It may also be desirable that the material have a high magnetic conductivity (relative permeability of approximately 1000). In some embodiments, the soft magnetic material may be implemented as Vacoflux 9CR, a Cobalt-Iron alloy commercially available from Vacuumschelze GmbH & Co. KG. Alternatively, a material from the same family or a soft magnetic ferrite could be used.

Tine head 120 also includes a concave bevel 150 along a plurality of edges to facilitate vibration, referred to hereinafter as a 'cusp.' The concave bevel 150 optimizes the moment of inertia of the tine head 120, provides a strong magnetic signal during the measurement phase, and displays an increase in sensitivity to changes in the parameter of interest in comparison to more conventional shapes (such as that of tine head 115) that is greater than expected. Other bevels may be employed that enjoy advantages such as ease of manufacture, increases in magnetic material, and so on. Particular choices in tine head design may therefore be contingent upon the particular application of the sensor.

Figure 3:
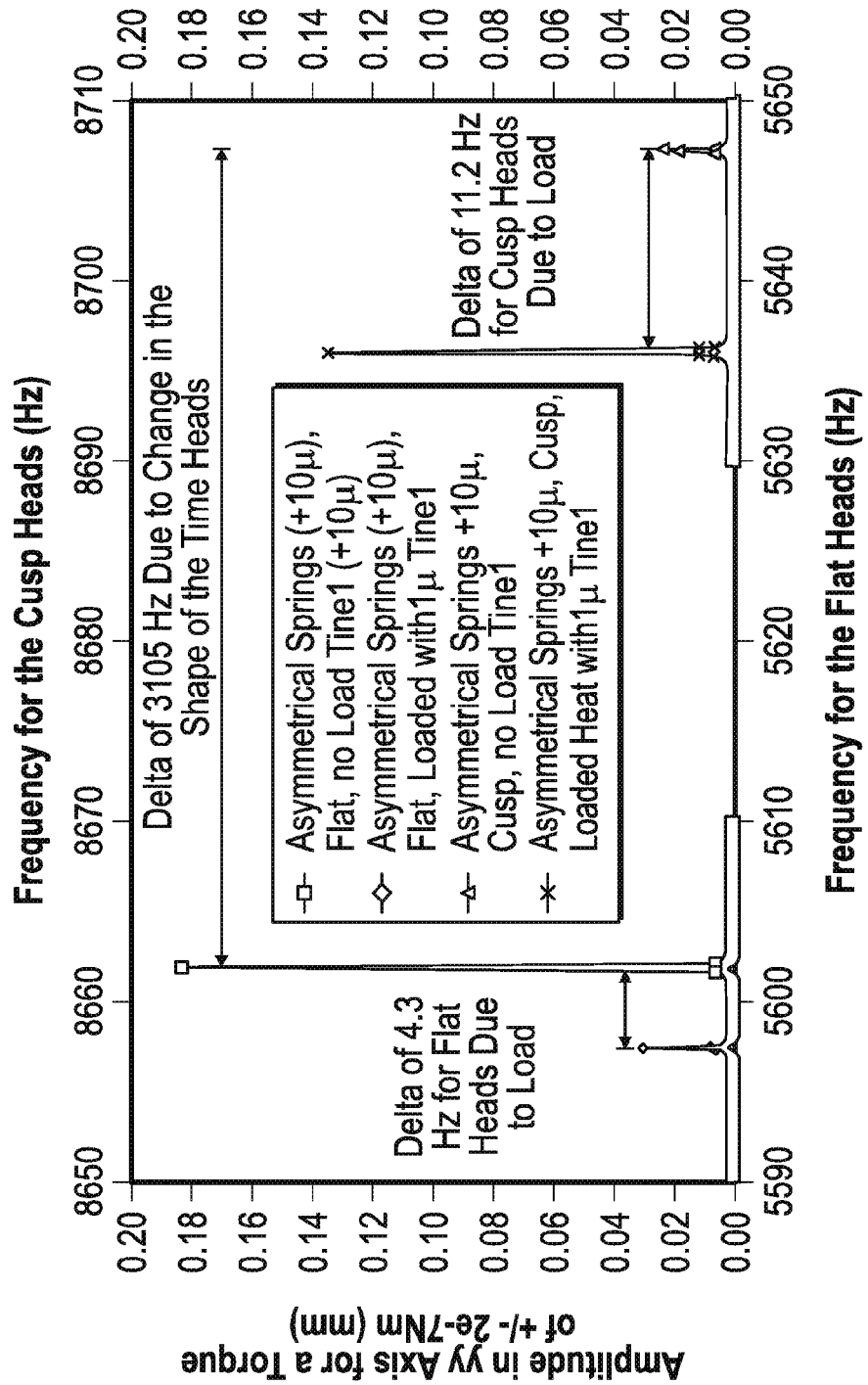
FIG. 3 shows a comparison of change in resonance frequency with changes in load for tine heads in accordance with embodiments of the present disclosure.

FIG. 3 shows a comparison of change in resonance frequency with changes in load for tine heads 115 and 120 in accordance with embodiments of the present disclosure. The cusped head 120 has a higher resonance frequency, and also has a higher change in resonance frequency (delta) for a given load increase in comparison to the conventional head 115. For an increase in mass of 1 micrometer, the cusp head has a change in frequency of 11.2 Hz, in comparison to a change of 4.3 Hz for the conventional head 115. Thus, introduction of the cusped head 120 results in an unpredicted increase in delta from the traditional head shape.

Figure 4:
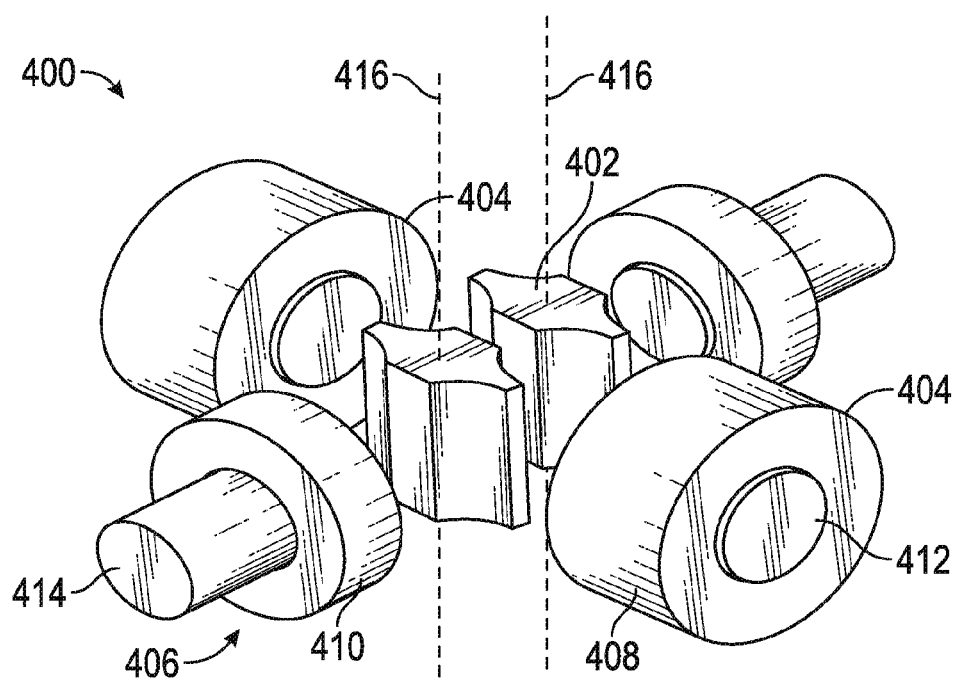
FIG. 4 shows a resonator assembly for determining a parameter of interest of a well fluid using resonant vibration in accordance with embodiments of the present disclosure.

FIG. 4 shows a resonator assembly for determining a parameter of interest of a well fluid from a subterranean formation using resonant vibration in accordance with embodiments of the present disclosure. The resonator assembly 400 includes a pair of substantially perpendicular soft magnetic tine heads 402 coupled via tine shafts (not shown), a switchable biasing assembly 404, and a switchable drive assembly 406. The switchable biasing assembly 404 comprises biasing coils 408 that, when energized by control electronics (not shown), provide a magnetic bias field that magnetizes the soft magnetic tine heads 402. The biasing coils 408 may be wrapped around a metallic core 412. The switchable drive assembly 406 includes driving coils 410, which may be wrapped around a metallic core 414.

When energized by control electronics, in some embodiments the driving coils 410 may act on the magnetized soft magnetic heads 402 to excite a torsional mode and cause resonant vibration of the tines. More particularly, coils 410 may have an axis that is perpendicular to a plane containing the tine axes 416. A current flowing through each coil 410 may generate a magnetic field producing a torque on each magnetic tine head 402 parallel to the corresponding tine axis. The coils 410 may be configured to produce a magnetic field with an axis orthogonal to both the longitudinal axes of the tines and the magnetic polarization vectors of the tine heads. An oscillating current flowing through the coils may exert opposite torques on the tine heads 402, causing them to rotate about their longitudinal axes.

Other configurations employing different orientations for at least one of the coils 408, the coils 410, or the tine heads 402; alternative switchable biasing assembly and/or switchable drive assembly designs; alternative modes of vibration; and various resonant characteristics will occur to those of skill in the art.

Current created by the tine movement may be used to monitor the motion of the tines. The torques of each tine head 402 may be in opposite rotational directions, so that when the tines torsionally oscillate, voltages are induced in the coils 410. These voltages may be proportional to angular velocity, and so may be read and interpreted to determine characteristics of torsional oscillation.

In particular embodiments, resonator assembly 400 may be implemented using tines 110 as described above. Thus, the soft magnetic tine heads 402, 120 are coupled via tine shafts 130. Due to the difference in cross sectional dimensions between the tine shafts 130 and the tine heads 402, 120, the resonator assembly 400 generates torsional motion predominantly in the thin shafts 130, while the significantly thicker terminal tine heads 402, 120 act as inertial masses.

Figure 5A:
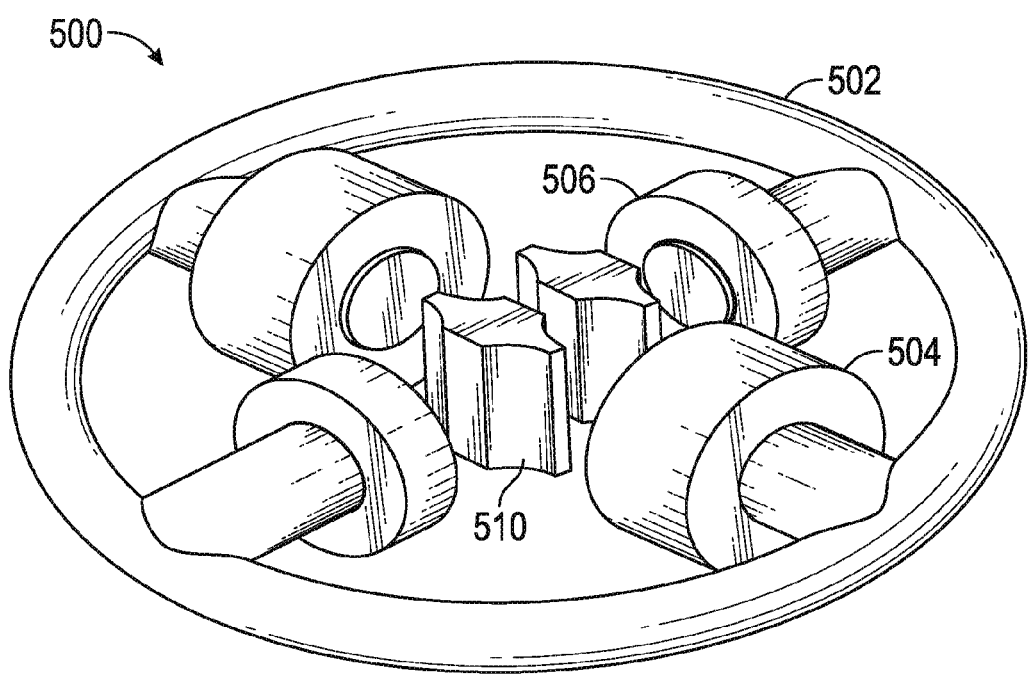
FIGS. 5A-5C show other resonator assemblies for determining a parameter of interest of a well fluid using resonant vibration in accordance with embodiments of the present disclosure.
Figure 5B:
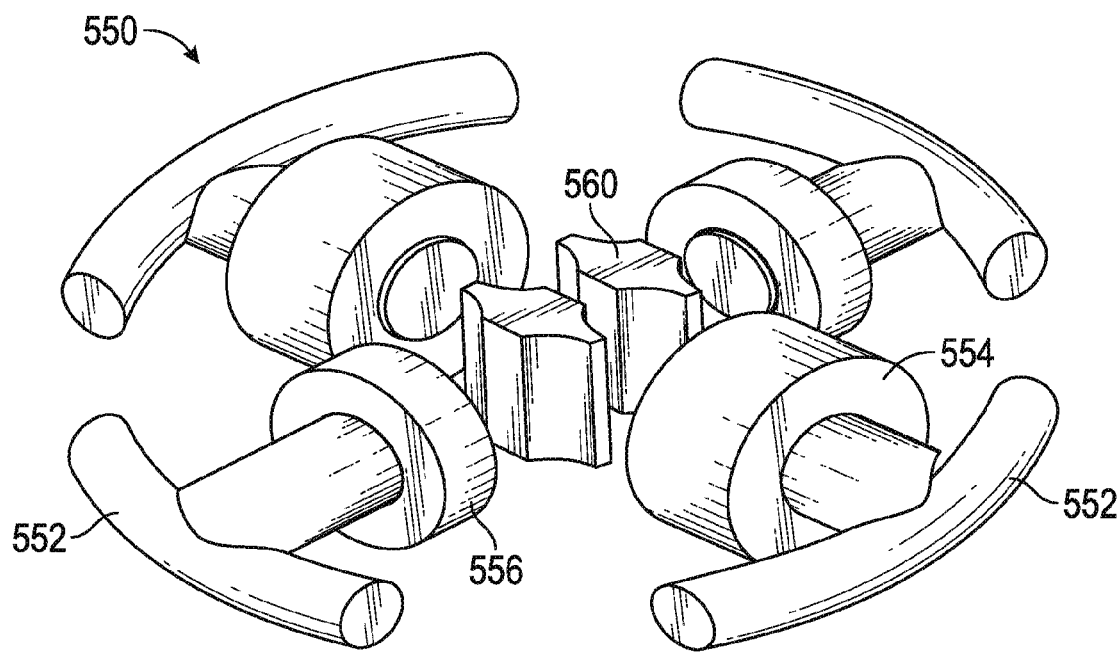
Figure 5C:
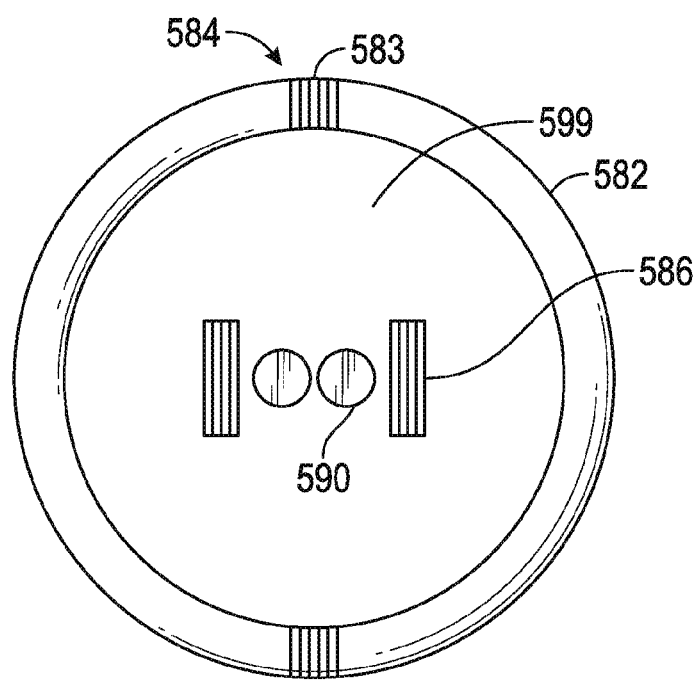

FIGS. 5A-5C show other resonator assemblies for determining a parameter of interest of a well fluid from a subterranean formation using resonant vibration in accordance with embodiments of the present disclosure. Referring to FIG. 5A, the resonator assembly 500 includes tine heads 510, switchable biasing assembly 504, and drive assembly 506 and a soft magnetic yoke 502 encircling them. Referring to FIG. 5B, the resonator assembly 550 includes a multi-part soft magnetic yoke 552. Switchable biasing assembly 554 and drive assembly 556 are positioned at a radial distance from the tine heads 560 less than the magnetic yoke 552. Although the switchable biasing assembly 554 and the drive assembly 556 are each shown positioned between the tine heads 560 and at least a portion of the soft magnetic yoke 552, one or more of the switchable biasing assembly 554 and the drive assembly 556 may be positioned askew from the soft magnetic yoke 552.

Referring to FIG. 5C, the resonator assembly 580 includes a soft magnetic yoke 582 with segments having coil windings 583 of the switchable biasing assembly 584 wrapped therearound. Drive assembly 586 may be positioned proximate the tine heads 590.

The yokes 502, 552, 582 are made of high magnetic conductive materials, which may be similar to the soft magnetic material 140 and have a central passage. The resonator assemblies may be configured to produce flux paths for at least one of the switchable biasing assembly and the drive assembly such that more than half of the total flux for the switchable biasing assembly and the drive assembly lies inside the central passage. A resonator assembly may be designed to use the yoke to modify the normal flux paths for the switchable biasing assembly and/or the drive assembly, such that more than half of the total flux for the switchable biasing assembly and the drive assembly lies inside the central passage 599. In turn, a resonator assembly may be configured to locate tine heads in the flux passing through the central passage. The soft magnetic yokes 502, 552, 582 may guide the static magnetic field to reduce the magnetic reluctance and limit the stray-field in the respective resonator assemblies 500, 550. Multiple yokes may be used in conjunction. Various configurations are possible.

Figure 6:
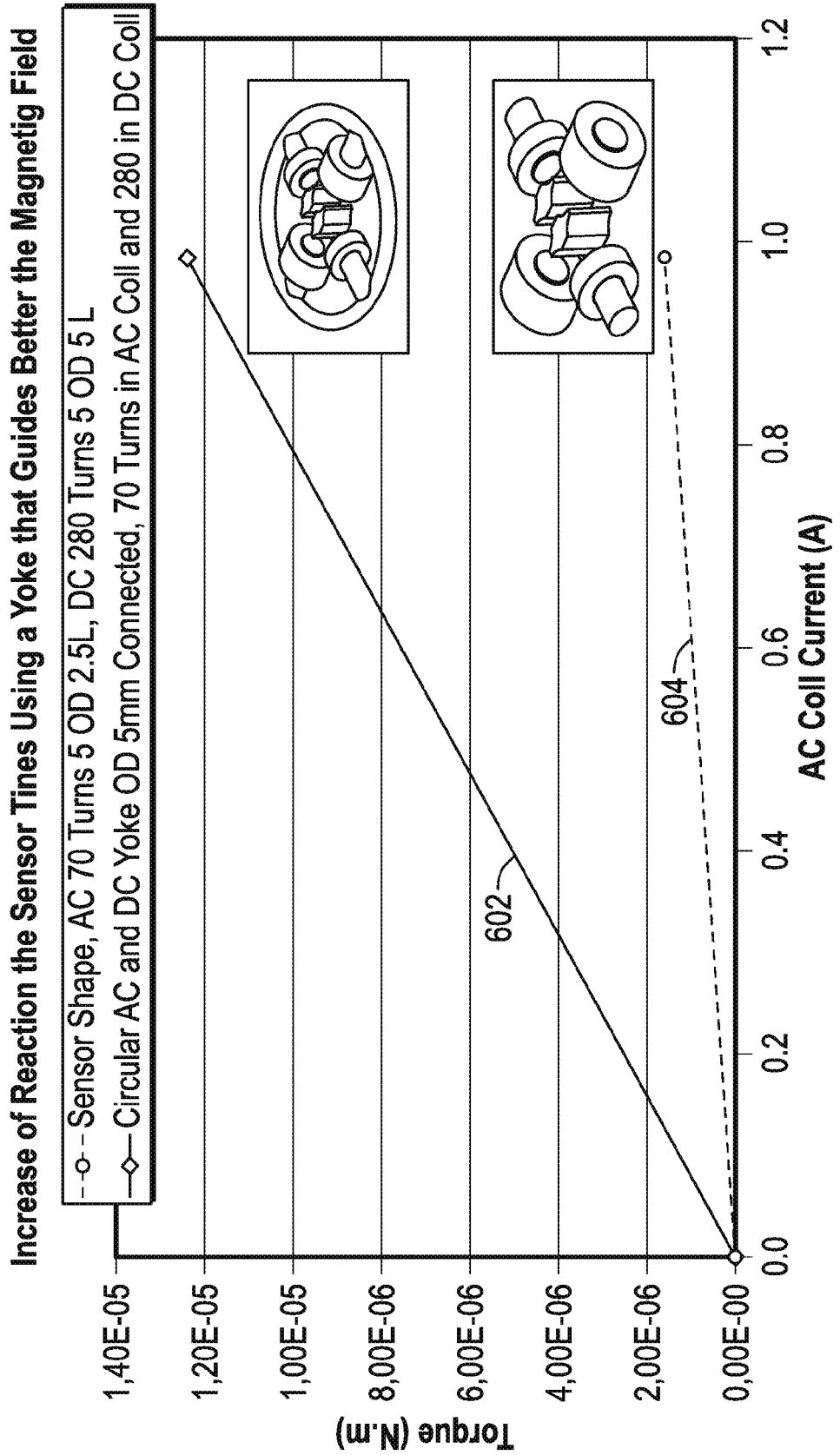
FIG. 6 shows a comparison of change in reaction torque with respect to coil current for yoked and unyoked resonant assemblies in accordance with embodiments of the present disclosure.

FIG. 6 shows a comparison of change in reaction torque with respect to coil current for the yoked and unyoked resonant assemblies in accordance with embodiments of the present disclosure. Both resonator assemblies include a cusped tine head. The driving coil for each is a 70 turn coil, while the biasing coil for each is a 280 turn coil. The response curve 602 of resonant assembly 500 has a higher torque for a given current to the drive assembly when compared to the response curve 604 of the resonator assembly without a soft magnetic yoke. The increase in torque between the yoked and unyoked assemblies is surprisingly large.

Figure 7A:
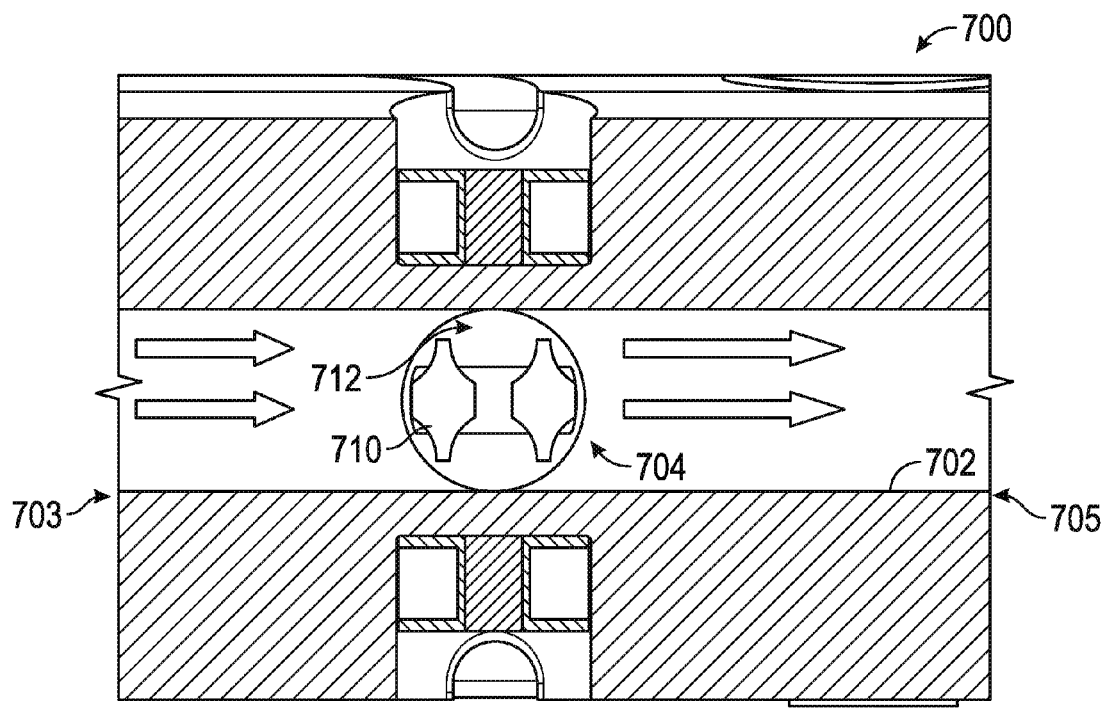
FIGS. 7A & 7B show devices for determining a parameter of interest of a well fluid using resonant vibration in accordance with embodiments of the present disclosure.
Figure 7B:
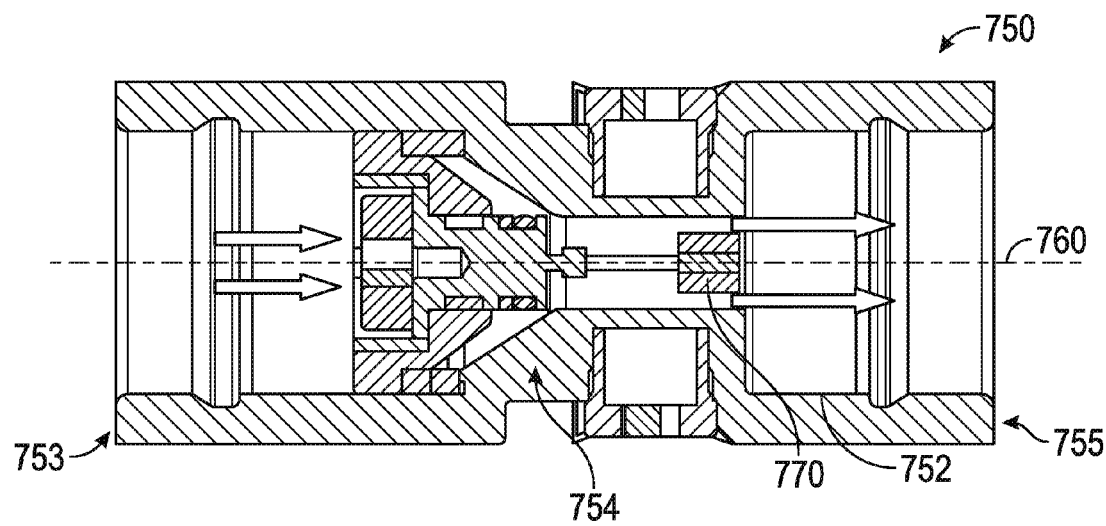

FIGS. 7A and 7B show devices for determining a parameter of interest of a well fluid from a subterranean formation using resonant vibration in accordance with embodiments of the present disclosure. Referring to FIG. 7A, device 700 includes a conduit 702 with a first end 703 and a second end 705, and a resonator assembly 704. The resonator assembly includes soft magnetic tine heads 710 in a flow of the fluid. The resonator assembly is conventionally oriented so that the flow of the fluid is perpendicular to the axis of the tines 712. Although this configuration may be convenient in terms of design, the arrangement creates an area with minimal fluid flow, and imperfect cleaning action may be anticipated.

Referring to FIG. 7B, device 750 includes a conduit 752 with a first end 753 and a second end 755, and a resonator assembly 754. The resonator assembly includes soft magnetic tine heads 770 in a flow of the fluid. The resonator assembly has an improved orientation which facilitates self-cleaning of the head via the fluid flow. The resonator assembly is oriented so that the flow of the fluid is substantially parallel to the tine axis 760, which allows the fluid flow to flush a greater portion of the surface of the sensor. This leads to a better cleaning of the sensitive areas of the sensor at the tine heads 770.

The teachings herein may be advantageously applied to a variety of systems in the oil and gas industry (including permanently deployed sensors in production settings), water wells, geothermal wells, surface applications and elsewhere. Merely for clarity, certain non-limiting embodiments will be discussed in the context of tools configured for wellbore uses.

Figure 8:
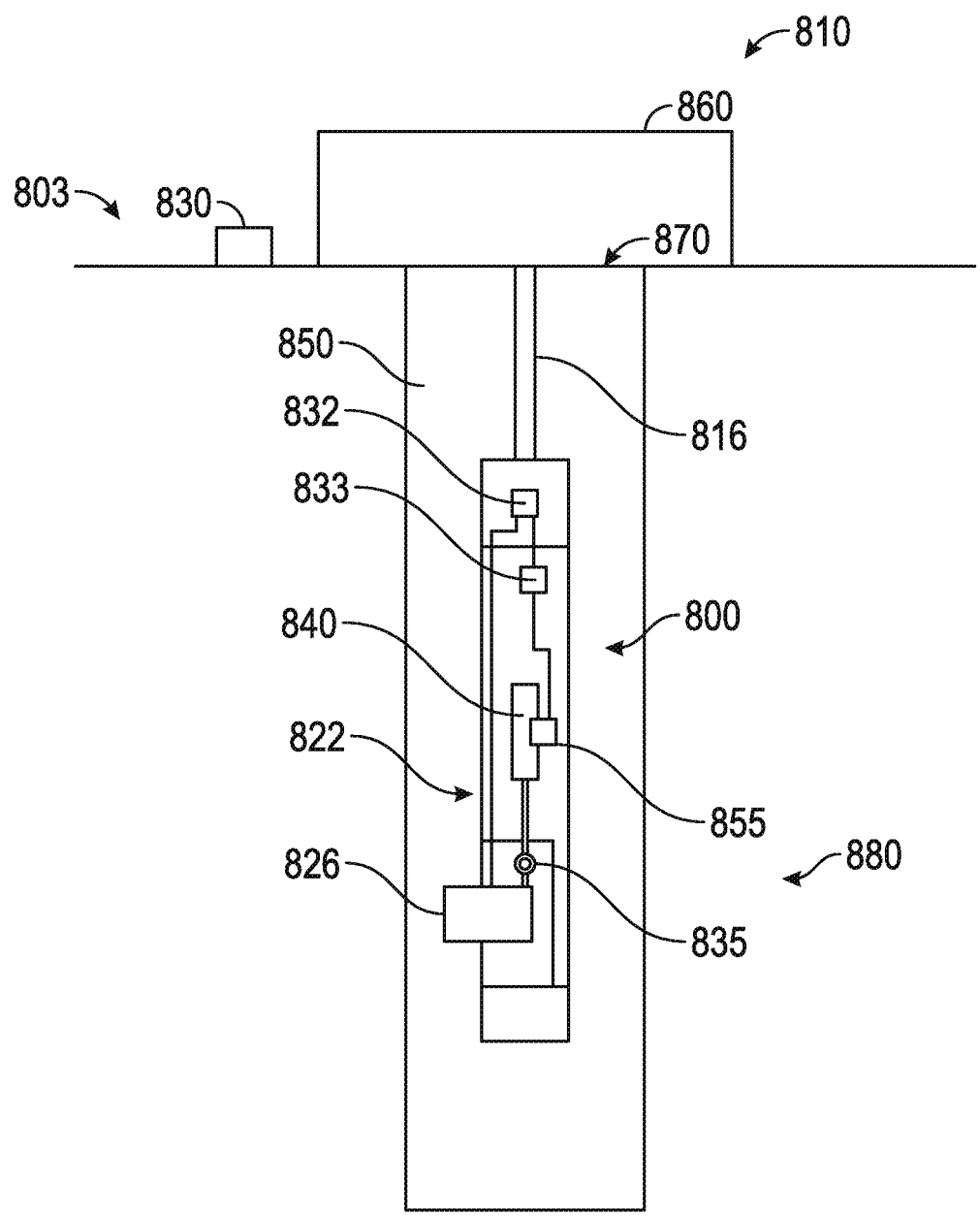
FIG. 8 shows a schematic illustration of a sampling system including a downhole tool in accordance with embodiments of the present disclosure.

FIG. 8 shows a schematic illustration of a sampling system including a downhole tool in accordance with embodiments of the present disclosure. The downhole tool 800 may be used to sample fluids from a desired location e.g., a hydrocarbon bearing reservoir. The system 810 may include a conventional derrick 860 erected on a derrick floor 870. A conveyance device 816 which may be rigid or non-rigid, may be configured to convey the downhole tool 800 into wellbore 850 (also called the borehole) in proximity to formation 880. Borehole 850 may intersect formation 880. The conveyance device 816 may be a drill string, coiled tubing, a slickline, an e-line, a wireline, etc. Downhole tool 800 may be coupled or combined with additional tools. Thus, depending on the configuration, the tool 800 may be used during drilling and/or after the wellbore 850 has been formed. While a land system is shown, the teachings of the present disclosure may also be utilized in offshore or subsea applications. The conveyance device 816 may include embedded conductors for power and/or data for providing signal and/or power communication between the surface and downhole equipment. For example, the conveyance device 816 can also provide communications between the downhole tool 800 and a surface controller 830 disposed at the surface of the earth 803. The conveyance device 816 may include a bottom hole assembly, which may include a drilling motor for rotating a drill bit. The earth formation 880 may include any subsurface material of interest such as a downhole fluid. The downhole tool 800 may include sensors for estimating parameters relating to the formation 880.

In order to operate the downhole tool 800 and/or provide a communications interface with the surface controller 830, the downhole tool 800 may include a downhole controller 832. In one embodiment, electronics (not shown) associated with the sensors may be configured to record information related to the parameters to be estimated. In some embodiments, the parameter of interest may be estimated using the recorded information.

In other embodiments, such electronics may be located elsewhere (e.g., at the surface). To perform estimation of a parameter during a single trip, the tool may use a "high bandwidth" transmission to transmit the information acquired by sensors to the surface for analysis. For instance, a communication line for transmitting the acquired information may be an optical fiber, a metal conductor, or any other suitable signal conducting medium. It should be appreciated that the use of a "high bandwidth" communication line may allow surface personnel to monitor and control the treatment activity in "real time."

In some embodiments, controllers 832, 833 may include mechanical, electromechanical, and/or electrical circuitry configured to control one or more components of the tool 800. In other embodiments, controllers 832, 833 may use algorithms and programming to receive information and control operation of the tool 800. Therefore, controllers 832, 833 may include an information processor that is data communication with a data storage medium and a processor memory. The data storage medium may be any standard computer data storage device, such as a USB drive, memory stick, hard disk, removable RAM, EPROMs, EAROMs, flash memories and optical disks or other commonly used memory storage system known to one of ordinary skill in the art including Internet based storage. The data storage medium may store one or more programs that when executed causes information processor to execute the disclosed method(s). Herein, "information" may include raw data, processed data, analog signals, and digital signals.

In embodiments of the present disclosure, the downhole tool 800 is a downhole fluid sampling tool including sensors for estimating parameters of a downhole fluid. Non-limiting examples of downhole fluids include drilling fluids, return fluids, formation fluids, production fluids containing one or more hydrocarbons, oils and solvents used in conjunction with downhole tools, water, brine, engineered fluids, and combinations thereof. The downhole tool 800 includes fluid tester 822 with a sensor 855 for estimating parameters of a downhole fluid such as, for example, density, viscosity, and/or other parameters. Fluid tester 822 is operatively connected to instrument controller 833 in order to operate the fluid tester 822 and/or provide a communications interface with other controllers. Instrument controller 833 may be incorporated into downhole controller 832, or may be associated with fluid tester 822. Sensor 855 may include, for example, a resonator assembly or other device including soft magnetic tine heads in accordance with the present disclosure.

In the embodiment depicted in FIG. 8, the fluid tester 822 includes collector 826 configured to gather a downhole fluid from outside of the tool for analysis downhole. For example, the collector 826 may extract wellbore fluids, formation fluid from the formation 880, and so on. The fluid tester 822 also includes a sample chamber 840.

The collector 826 includes a fluid mover 835 that sends a sample of the gathered downhole fluids to the sample chamber 840, where sensor 855 takes measurements of the sample. The sensor 855 is in contact with the sample in the sample chamber 840. For example, in the case of a resonator assembly, a portion of the magnetic tine head is immersed in the downhole fluid in the sample chamber. Switching between activation and deactivation of the biasing assembly and drive assembly, along with control of the sensor 855 generally, may be performed by downhole controller 832 or instrument controller 833.

In some embodiments, controllers 832, 833 may include mechanical, electromechanical, and/or electrical circuitry configured to control one or more components of the tool 800. In other embodiments, controllers 832, 833 may be implemented in a hardware environment as described below, and use algorithms and programming to receive information and control operation of the tool 800.

The downhole controller 832 and instrument controller 833 may use preprogrammed commands, commands from the surface controller, or combinations of these to control downhole components of tool 800, including the sensor 855.

Tool 800 may include embodiments with elastomeric pads urged against the borehole wall, or may draw fluid from the annulus between the borehole wall and the tool. Other embodiments may sample fluid moving continuously through a flow line. In particular embodiments, the fluid mover may be a single-action or dual action piston pump. The pumps may be energized by the same power source or independent power sources. The power source may be electric, hydraulic, pneumatic, etc. Magnetic particles may be removed by flushing the magnetic tine using an engineered fluid. The tool 800 may include anchoring, stabilizing and sealing elements disposed on a drill string, such as grippers and packers.

In some arrangements, the sampling event may be human initiated. For example, sensors may transmit signals representative of one or more selected operating parameters to the surface. Based on these measurements, a human operator may initiate a sampling event. In other arrangements, controllers 830, 832 may be used, alone or in combination, to control the operation of tool 800 to ensure that sample retrieval occurs at desired times and/or at specified conditions.

Figure 9:
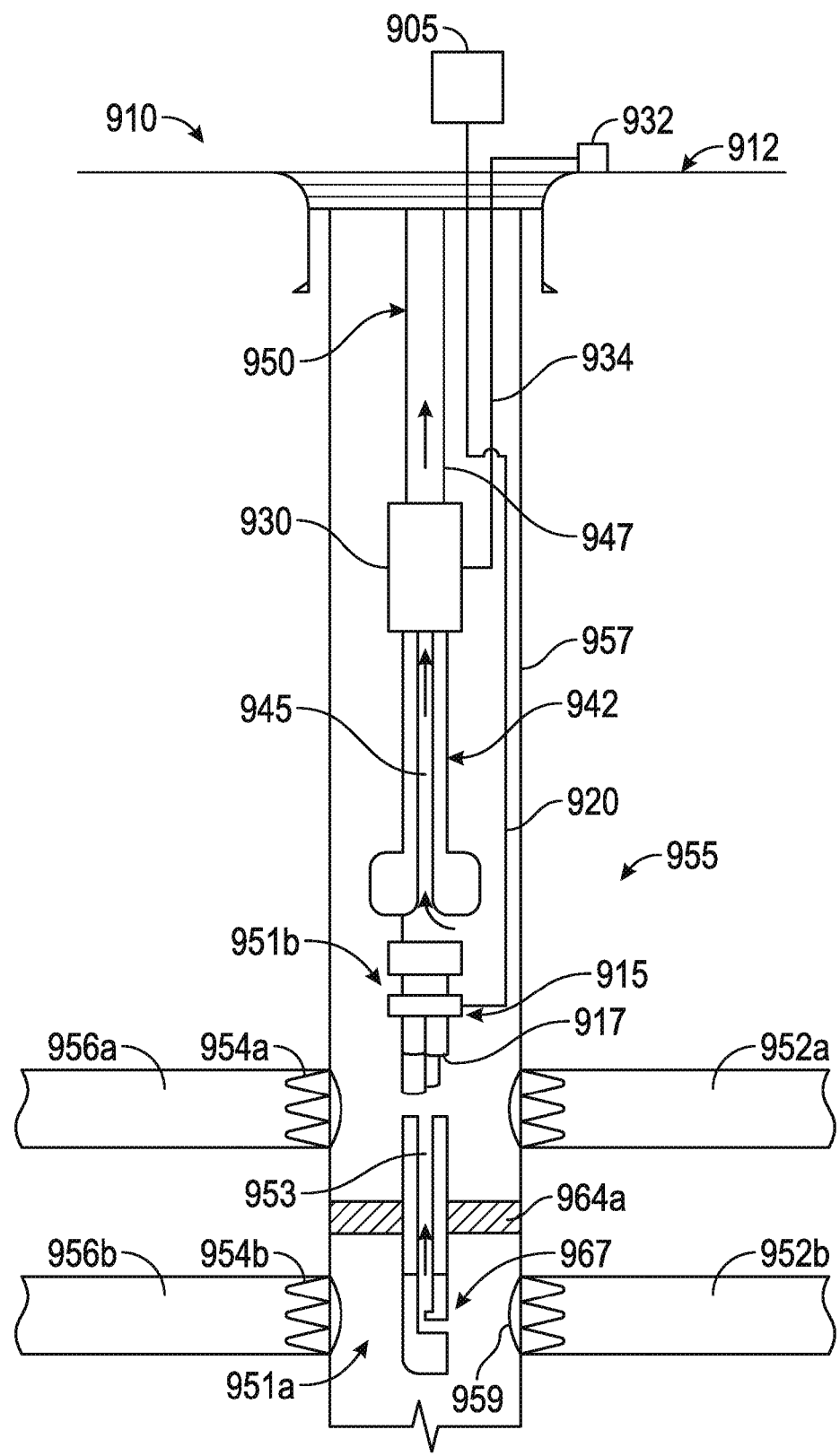
FIG. 9 shows a schematic illustration of a production system including a device in accordance with embodiments of the present disclosure.

FIG. 9 shows a schematic illustration of a production system including a device in accordance with embodiments of the present disclosure. FIG. 9 shows a well 950 that produces formation fluids 956a and 956b including hydrocarbons from two exemplary production zones, 952a (upper production zone) and 952b (lower production zone), respectively, in a formation 955. Casing 957 lines the well. Perforations 954a adjacent the upper production zone 952a and perforations 954b adjacent the lower production zone 952b facilitate recovery of formation fluids. A packer 964a positioned above (uphole) of the lower production zone perforations 954a isolates the lower production zone 952b from the upper production zone 952a. A screen 959 inhibiting solids, such as sand, from entering into the wellbore may be installed adjacent the perforations.

The formation fluid 956b from the lower production zone 952b enters the annulus 951a of the well 950 through the perforations 954a and into a tubing 953 via a flow control valve 967. The formation fluid 956a from the upper production zone 952a enters the annulus 951b (the annulus portion above the packer 964a) via perforations 954a. The formation fluid 956a enters production tubing or line 945 via inlets 942.

In cases where the formation pressure is not sufficient to push the fluid 956a and/or fluid 956b to the surface, an artificial lift mechanism, such as an electrical submersible pump (ESP) or other lift system may be utilized to lift the fluids from the well to the surface 912. ESP 930 receives formation fluids 956a and 956b and pumps the fluids via tubing 947 to the surface 912. Two-way data communication may be provided between ESP 930 and ESP control unit 932 by cable 934. ESP control unit 932 may control the operation of ESP 930. ESP control unit 932 may include a processor configured to analyze and control the operations of ESP 930. ESP control unit 932 may be configured to alter pump speed of the ESP by sending control signals in response to data or instructions received from another controller.

Data communication lines run inside the well 950 to operate the various devices in the well 950 and to obtain measurements and other data from the various sensors in the well 950. A variety of other sensors may be placed at suitable locations in the well 950 to provide measurements or information relating to a number of downhole parameters of interest.

One or more gauge or sensor carriers, such as a carrier 915, may be placed in the production tubing to house any number of suitable sensors. The carrier 915 includes permanent well monitoring sensor 917 comprising resonator assemblies or other devices in accordance with embodiments of the present disclosure (such as device 750) for estimating characteristics of the production fluid such as density, viscosity, and so on. Data communication line 947 may transmit data from permanent well monitoring sensor 917 to well controller 905 at the surface 912. Well controller 905 may include electrical circuitry configured to control one or more components of the system 900. In other embodiments, 905 may be implemented in a hardware environment as described below, and use algorithms and programming to receive information and control operation of the production system 900, such as for example, controlling ESP 930.

Figure 10:
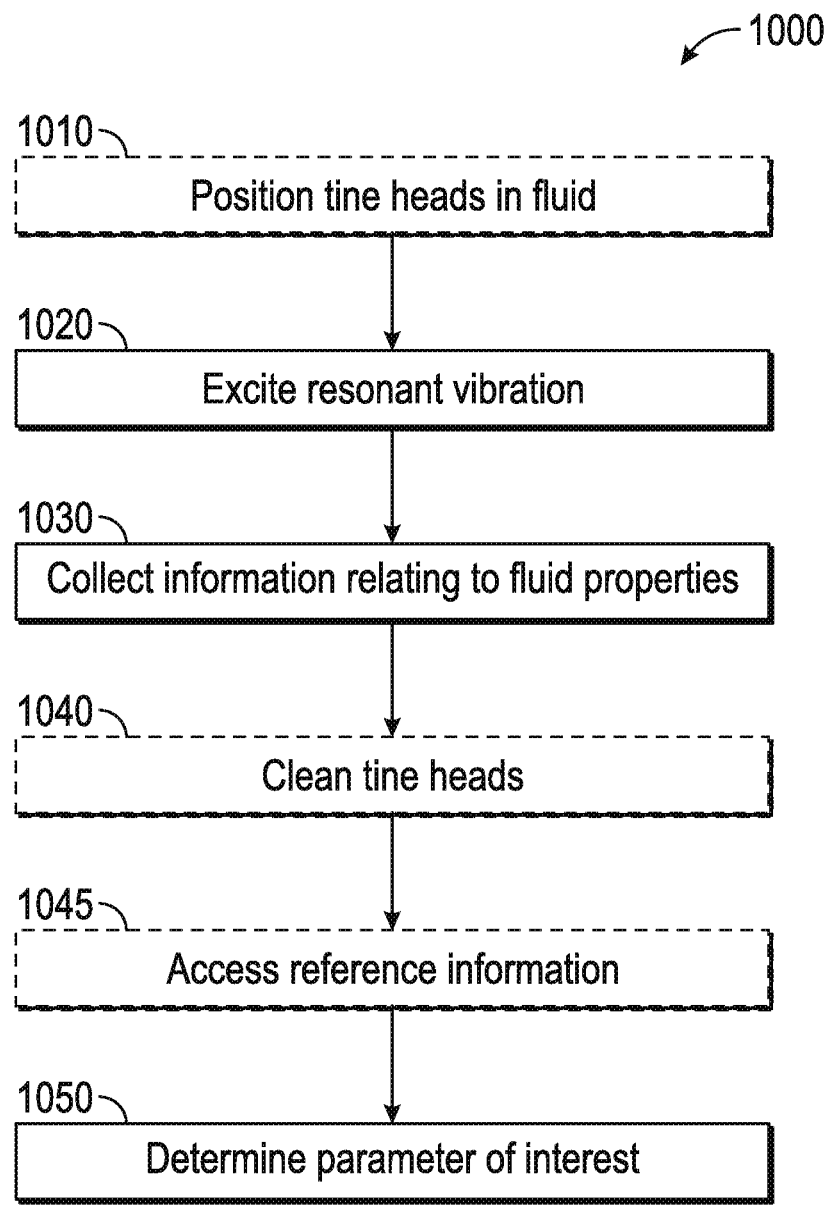
FIG. 10 shows, in flow chart form, one method according to the present disclosure for evaluating a well fluid from a formation intersected by a borehole.

FIG. 10 shows, in flow chart form, one method 1000 according to the present disclosure for evaluating a well fluid from a formation intersected by a borehole. Method 1000 may include optional step 1010, positioning soft magnetic tine heads of a resonator in accordance with the present disclosure in the fluid. The resonator may include at least two substantially parallel resonant tines structurally coupled to behave as a single resonator, with each resonant tine of the at least two substantially parallel resonant tines including a soft magnetic resonant tine head comprising soft magnetic material uncontained by a supporting surface. The soft magnetic heads may be switchable between a magnetic state producing a magnetic field and a non-magnetic state producing substantially no magnetic field.

Step 1010 may be carried out by conveying a downhole fluid testing tool into a borehole filled with downhole fluid. At step 1020, the method includes exciting resonant vibration in the tines of the resonator. Step 1020 may include magnetizing the soft magnetic resonant tine heads and driving the heads with an oscillating field. Step 1020 may be carried out by activating a switchable biasing assembly to provide a magnetic bias field that magnetizes the tines of the resonator, and activating a switchable drive assembly to act on the magnetized soft magnetic heads to cause resonant vibration of the magnetized soft magnetic heads.

At step 1030, information relating to properties of the fluid is measured. Step 1030 may include sensing the vibration of the resonator assembly. Step 1030 may include sensing vibration of the magnetized soft magnetic heads in a flow of the downhole fluid.

Optional step 1040 comprises cleaning the soft magnetic heads. Step 1040 may be carried out by deactivating the switchable biasing assembly produce Gaussian demagnetization of the soft magnetic heads. Step 1040 may further include removing the adhered particles using a fluid. The fluid may be at least one of: i) the downhole fluid; and ii) engineered fluid.

At step 1050, the information (e.g., a sensed response indicative of the vibration) is used to determine the parameter of interest. The information may be applied to a model relating sensor information to the parameter of interest, and may also include comparison or combination of the information with reference information about the formation or about particular fluids. In some embodiments, method 1000 may include step 1045, where reference information generally is accessed.

In support of the teachings herein, various analysis components may be implemented in a hardware environment. For example, electronics, controllers, sensors, and the like may include a digital and/or analog hardware environment. Herein, the term "information" may include one or more of: raw data, processed data, and signals.

The term "conveyance device" or "carrier" as used in this disclosure means any device, device component, combination of devices, media and/or member that may be used to convey, house, support or otherwise facilitate the use of another device, device component, combination of devices, media and/or member. Illustrative conveyance devices include wirelines, wireline sondes, slickline sondes, e-lines, jointed drill pipe, coiled tubing, wired pipe, casing, completion tools, liners, drop tools, and so on.

As used herein, the term "fluid" and "fluids" refers to one or more gasses, one or more liquids, and mixtures thereof. "Hydrocarbon fluid" refers to a fluid containing at least one hydrocarbon. Well fluid refers to fluids relating to a well intersecting a subterranean earth formation. Well fluid from a subterranean formation may refer to either a fluid in a formation or a borehole intersecting a formation; a fluid recovered from a formation or a borehole intersecting a formation; fluids introduced to well; or otherwise related to the well, e.g., as part of exploration, development, completion, or production. A "downhole fluid" as used herein includes any gas, liquid, flowable solid and other materials having a fluid property, and relating to hydrocarbon recovery. A downhole fluid may be natural or man-made and may be transported downhole or may be recovered from a downhole location. Non-limiting examples of downhole fluids include drilling fluids, return fluids, formation fluids, production fluids containing one or more hydrocarbons, oils and solvents used in conjunction with downhole tools, water, brine, and combinations thereof. Well fluids may include, any of hydrocarbon fluids, downhole fluids, stimulation fluids, fracking fluids, additives for oil field fluids, mud filtrates, completion fluids, cement slurries, and so on. "Engineered fluid" may be used herein to mean a fluid formulated for cleaning the soft magnetic tine heads. The engineered fluid may be stored separately from downhole fluids. "Coating," in contrast with a supporting surface, may be defined herein as an applied material with a thickness of less than 0.5 millimeters.

By substantially no magnetic field, it is meant magnetic field at a level sufficiently low to allow a portion of particles to fall off such that the soft magnetic tine head may be used indefinitely continuously with periodic cleaning without decline in effectiveness, examples of such a portion including, for example, at least 95 percent, at least 99 percent, at least 99.9 percent, at least 99.99 percent, and so on, up to and including all particles, with examples of such a magnetic force including, for example, fewer than 1 millitesla, 0.5 millitesla, 0.1 millitesla, and so on, down to and including zero magnetic pull. "Uncontained by a supporting surface" may be defined as lacking any non-soft magnetic material surrounding the soft magnetic material for the purpose of maintaining the relative location of the soft magnetic material with respect to the tines or otherwise structurally or mechanically supporting the soft magnetic material during vibration. Substantially continuous material composition may be defined as having a homogeneous composition other than a minor portion such that function of the soft magnetic tine head is virtually indistinguishable from single material composition, examples of such a portion including, for example, at least 5 percent, 1 percent, less than 0.1 percent, less than 0.01 percent, and so on, down to and including no additional material. In contrast to supporting surfaces, a coating is a non-structural application to soft magnetic materials.

As used herein, a processor is any information processing device that transmits, receives, manipulates, converts, calculates, modulates, transposes, carries, stores, or otherwise utilizes information. In several non-limiting aspects of the disclosure, an information processing device includes a computer that executes programmed instructions for performing various methods. These instructions may provide for equipment operation, control, data collection and analysis and other functions in addition to the functions described in this disclosure. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on.

While the foregoing disclosure is directed to the one mode embodiments of the disclosure, various modifications will be apparent to those skilled in the art. It is intended that all variations be embraced by the foregoing disclosure.

What is claimed is:

1. An apparatus for determining a parameter of interest of a well fluid relating to a well intersecting a subterranean formation using resonant vibration, the apparatus comprising:
    a resonator assembly comprising:
    a plurality of resonant tines structurally coupled to behave as a single resonator, at least one resonant tine of the plurality of resonant tines having a longitudinal axis along a direction of elongation of the at least one resonant tine and including:
        a soft magnetic tine head comprising soft magnetic material uncontained in a direction non-parallel to the longitudinal axis by a supporting surface, and
        a tine shaft;
    wherein the at least one resonant tine has a cross section perpendicular to the longitudinal axis of the tine at the tine head, where the cross section at the tine head has a substantially continuous material composition.

2. The apparatus of claim 1, wherein each corresponding tine of the plurality of resonant tines is formed by at least the resonant tine head and a tine shaft; and wherein each corresponding tine has a cross section perpendicular to a longitudinal axis of the corresponding tine, the cross section including a tine head, where the cross section has a substantially continuous material composition unconstrained.

3. The apparatus of claim 1, wherein each corresponding tine of the plurality of resonant tines is formed by at least the tine head and a tine shaft; and the tine shaft terminates at the tine head.

4. The apparatus of claim 1 wherein the soft magnetic material has a compressive strength of at least 200 MPa.

5. The apparatus of claim 1 wherein the resonator assembly comprises:

a switchable biasing assembly that, when activated, provides a magnetic bias field that magnetizes the soft magnetic tine head of the at least one resonant tine; and a switchable drive assembly that, when activated, acts on the magnetized soft magnetic head of the at least one resonant tine to cause resonant vibration of the magnetized soft magnetic head of the at least one resonant tine; and the apparatus further comprises a processor configured to:

activate the switchable biasing assembly and the drive assembly;

sense the vibration of the magnetized soft magnetic tine head of the at least one resonant tine in a flow of the downhole fluid; and determine the parameter based on the sensed vibration.

6. The apparatus of claim 5 comprising a magnetic yoke having a central passage, wherein the apparatus is configured to produce flux paths for at least one of the switchable biasing assembly and the drive assembly such that more than half of the total flux for the switchable biasing assembly and the drive assembly lies inside the central passage.

7. The apparatus of claim 5 comprising at least one magnetic yoke, wherein at least one of the switchable biasing assembly and the drive assembly is positioned between the tine heads and at least a portion of the at least one magnetic yoke.

8. The apparatus of claim 5 comprising at least one magnetic yoke encircling the switchable biasing assembly, the drive assembly, and the soft magnetic resonant tine heads.

9. The apparatus of claim 5 comprising at least one magnetic yoke, wherein the magnetic yoke acts on the magnetic field of the drive assembly to increase torque acting on the soft magnetic resonant tine head of the at least one resonant tine during the resonant vibration.

10. The apparatus of claim 5 comprising at least one magnetic yoke, wherein the magnetic yoke acts on a magnetic field of the switchable biasing assembly.

11. The apparatus of claim 10 wherein the magnetic yoke acts on a static magnetic field of the switchable biasing assembly to increase magnetization on the soft magnetic resonant tine head of the at least one resonant tine during activation of the biasing assembly.

12. The apparatus of claim 1 wherein the tines are substantially parallel.

13. The apparatus of claim 1 comprising a coating for the soft magnetic resonant tine heads.

14. The apparatus of claim 1 comprising a conduit, wherein while the apparatus is immersed in the fluid, the fluid enters a first end of the conduit and flows along the conduit to a second end of the conduit, and the soft magnetic resonant tine head of the at least one resonant tine is in a flow of the fluid in the conduit.

15. The apparatus of claim 14 wherein the soft magnetic tine head of the at least one resonant tine is oriented so that the longitudinal axis of the tines is substantially parallel to the flow of the fluid.

16. A method of determining a parameter of interest of a well fluid from a subterranean formation using resonant vibration, the method comprising:

activating a switchable biasing assembly to provide a magnetic bias field that magnetizes at least one soft magnetic tine head coupled to a corresponding at least one resonant tine of a plurality of resonant tines structurally coupled to behave as a single resonator, each corresponding at least one resonant tine having a longitudinal axis along a direction of elongation of the at least one resonant tine and including:

a soft magnetic tine head comprising soft magnetic material uncontained by a supporting surface in a direction non-parallel to the longitudinal axis, and a tine shaft;

wherein each corresponding at least one resonant tine has a cross section perpendicular to the longitudinal axis of the tine at the tine head, where the cross section at the tine head has a substantially continuous material composition;

activating a switchable drive assembly to act on the at least one magnetized soft magnetic head to cause resonant vibration of the at least one magnetized soft magnetic head;

sensing the vibration of the at least one magnetized soft magnetic head in a flow of the downhole fluid; and determining the parameter based on the sensed vibration.

17. The method of claim 16 further comprising cleaning the magnetized soft magnetic heads by Gaussian demagnetization caused by deactivating the switchable biasing assembly.

18. The method of claim 17 wherein cleaning the soft magnetic tine heads further comprises removing particles using a fluid comprising at least one of: i) the downhole fluid; and ii) engineered fluid.

19. The method of claim 17 wherein the soft magnetic heads are switchable between a magnetic state producing a magnetic field and a non-magnetic state producing substantially no magnetic field.

20. The method of claim 16 wherein the downhole fluid comprises production fluid.

* * * * *